United States Patent [19]

Begum et al.

[11] Patent Number: 4,713,246

[45] Date of Patent: Dec. 15, 1987

[54] ETOPOSIDE ORAL DOSAGE FORM

[75] Inventors: Selima Begum; Ismat Ullah; Bernard C. Nunning, all of Liverpool, N.Y.

[73] Assignee: Bristol-Myers Company, New York, N.Y.

[21] Appl. No.: 847,147

[22] Filed: Apr. 2, 1986

Related U.S. Application Data

[63] Continuation of Ser. No. 742,644, Jun. 10, 1985, abandoned, which is a continuation of Ser. No. 591,144, Mar. 19, 1984, abandoned.

[51] Int. Cl.$^4$ .................. C07H 15/20; C07H 15/24; C07D 317/44; A61K 9/42
[52] U.S. Cl. .................................. 424/455; 424/456; 514/27; 514/33; 536/18.1; 549/298
[58] Field of Search .................. 536/18.1; 514/27, 33; 549/298; 424/455, 456

[56] References Cited

U.S. PATENT DOCUMENTS

| | | | |
|---|---|---|---|
| 3,408,441 | 10/1968 | Wartburg et al. | 424/180 |
| 3,524,844 | 8/1970 | Keller-Juslen et al. | 536/18.1 |
| 4,567,253 | 1/1986 | Durst et al. | 549/298 |

FOREIGN PATENT DOCUMENTS

| | | | |
|---|---|---|---|
| 6617379 | 6/1967 | Netherlands | 536/18.1 |
| 0481097 | 12/1969 | Switzerland | 536/18.1 |
| 1205966 | 9/1970 | United Kingdom | 536/18.1 |

OTHER PUBLICATIONS

Falkson et al, Cancer, Apr. 1975, vol. 35(4), pp. 1141–1144.
D'Incalci et al., Pharmacokinetics of VP16-213, Given by Different Administration Methods, Chem. Abstracts 97:275w, (1982).
Westergaard et al., The Mechanism Whereby Bile Acid Micelles Increase the Rate of Fatty Acid and Cholesterol Uptake into the Intestinal Mucosal Cell, Chem. Abstracts 85:75523m, (1976).
Bates et al., Solubilizing Properties of Bile Salt Solutions . . . on . . . Glutethimide, Griseofulvin, and Hexestrol, Chem. Abstracts 64:9517e (1966), 65:15165a (1966).
Bates et al., Rates of Dissolution of Griseofulvin and Hexestrol in Bile Salt Solutions, Chem. Abstracts 65:8680b, (1966).
Malone et al., Deoxycholic Acid Enhancement of Orally Administered Reserpine, Chem. Abstracts 65:14303e, (1966).
NCI Investigational Drugs—Phar. Data, 1981, pp. 117–119, NIH Publication No. 81-2141.
Cancer Chemotherapy and Pharmacology, (1982), 7:141–145.
Jour. of Pharm. Sciences, (Bates et al.), 55, 191–199, (1966).
Jour. of Pharm. Sciences, (Malone et al.), 55, 972–974, (1966).
Jour. of Clinical Investigation, (Westergaard et al.), 58, 97–108, (1976).

*Primary Examiner*—Ronald W. Griffin
*Attorney, Agent, or Firm*—Lester E. Johnson

[57] ABSTRACT

A liquid dosage form suitable for oral administration of etoposide which is sufficiently concentrated to be administered in capsule form and which provides improved absorption of the drug relative to prior oral formulations.

11 Claims, No Drawings

ETOPOSIDE ORAL DOSAGE FORM

This application is a continuation of application Ser. No. 742,644, filed June 10, 1985, now abandoned which is a continuation of application Ser. No. 591,144, filed Mar. 19, 1984, now abandoned.

FIELD OF THE INVENTION

The present invention refers to a drug bio effecting and body treating composition having a glycosidic active ingredient.

DESCRIPTION OF THE PRIOR ART

Etoposide is a semi-synthetic product derived from podophyllotoxin. The material is identified by the chemical name 4'-demethylepipodophyllotoxin9-(4,6-O(R)-ethylidene-beta-D-glucopyranoside). It is referred to in the literature as VP-16-213, VePesid ®, Ethylidene-Lignan P, and EPEG. It has been evaluated for use in treatment of cancer under the auspices of The National Cancer Instutute under the number NSC-141540. It has recently been approved by the Federal Food and Drug Administration for use in the treatment of refractory testicular cancer and has been proposed for use in the treatment of small cell lung cancer.

In investigations conducted under the auspices of the National Cancer Institute, the drug was supplied as a solution for injection having the following composition: etoposide, 100 mg; citric acid, anhydrous 10 mg; benzyl alcohol, 150 mg; polysorbate 80, purified, 400 mg; polyethylene glycol 300, 3.25 g; alcolhol, absolute as 5.12 g. Each ampule of the foregoing composition consisted of 5 ml of solution which was diluted 20 to 50 times with 0.9% sodium chloride or 5% dextrose for injection before administration by slow intravenous infusion.

When the foregoing intravenous composition was administered by ingestion rather than injection, the 5 ml ampule was either taken as a teaspoon dose form or first diluted with water, it was found that the bioavailability by the oral route was approximately 90% that by the intravenous route (M.D'Incalci et al., Cancer Chemotherapy and Pharmacology (1982) 7:141–145). A similar dose taken by capsule in which 100 mg of active ingredient was contained in approximately 1.3 ml of encapsulated solution in which the vehicle consisted of polyethylene glycol 400, glycerine, water, and citric acid yielded only about one-half the bioavailability of the intravenous solution when taken by ingestion (M.D'Incalci et al., loc. cit.). The present invention addresses this problem of reduced bioavailability of the capsule dosage form, and provides a liquid formulation of sufficiently high concentration for encapsulation which affords bioavailability upon ingestion equal to the intravenous solution.

SUMMARY OF THE INVENTION

The present invention takes advantage of our discovery that taurocholic acid when included in a solution dosage composition with etoposide results in markedly improved absorption of the drug following ingestion of the composition. It is believed that this is due to the formation of a micellar solution of etoposide on dilution thereof with the gastric contents.

In investigating this problem, we have found that the capsule formulation referred to above when mixed with water in the proportion of about 10 ml of water per 100 mg of etoposide results in the immediate formation of a heavy, milky white precipitate. When as little as an equal weight of taurocholic acid relative to the etoposide is included in the liquid capsule formulation, precipitate formation is delayed for over an hour on mixing the formulation with 10 ml of water. The following tabulation illustrates this effect of taurocholic acid and other bile acids.

EFFECT OF ADDED BILE ON PRECIPITATE FORMATION

| Experiment No. | Bile Acid or Salt | Amount of* Etoposide (mg) | Amount of Bile Acid/ Salt (mg) | Precipitate Formation Time (hr) | Solution pH |
|---|---|---|---|---|---|
| 1 | Taurocholic | 200 | 1000 | 1.5 | |
| 2 | Acid | 200 | 500 | 1.0 | |
| 3 | | 100 | 1000 | 21.0 | 4.7 |
| 4 | | 100 | 500 | 5.0 | |
| 5 | | 100 | 200 | 2.0 | |
| 6 | | 100 | 100 | 1.5 | |
| 7 | | 100 | 10 | Instantaneous | |
| 8 | Sodium | 200 | 1000 | >24 | |
| 9 | Cholate | 200 | 500 | 1.0 | 10.9 |
| 10 | | 100 | 1000 | >24 | |
| 11 | | 100 | 500 | 4.0 | |
| 12 | Sodium | 200 | 1000 | >24 | |
| 13 | Deoxycholate | 200 | 500 | >24 | 11.0 |

*Supplied as a solution having the following composition:
etoposide, micronized      100.0 mg.
polyethylene glycol 400   1084.0 mg.
glycerol                    81.5 mg.
water                       77.6 mg.
citric acid                  2.0 mg.

Surface tension measurements on the aqueous dilutions of the bile acid formulations referred to in the foregoing table have confirmed that, indeed, micellar solutions of etoposide are produced. This is reflected in the failure for a further decrease in surface tension to occur as the concentration of taurocholic acid in the solution is increased. That concentration where no further decrease in surface tension occurs is referred to as critical micellar concentration.

The phenomenon of micellar solubilization of poorly water-soluble drugs mediated by bile acids, including taurocholic acid, has been previously reported with respect to griseofulvin, hexesterol, glutethimide (Bates et al., Journal of Pharmaceutical Sciences, 55, 191-199), reserpine, Malone et al., ibid. 55, 972-974 (1966), fatty acids, and cholesterol (Westergaard et al., Journal of Clinical Investigation, 58, 97-108 (1976)).

DETAILED DESCRIPTION OF THE INVENTION

The present invention involves a pharmaceutical solution of etoposide which has the unique property of providing a stable apparent solution of the drug upon dilution thereof with from 1 to 100 volumes of water. The solution is stable and free of precipitate for a period of at least two hours sufficient to permit administration to and absorption by the mammalian organism. It has been found that the bioavailability of etoposide following oral administration of the present dosage form is substantially equivalent to that achieved by intravenous administration of a solution of a drug. It is believed that ingestion of the present dosage form and resulting dilution thereof by the stomach contents results in the formation of a micellar solution of etoposide in the stomach which is readily absorbed by the gastrointestinal tract. Applicants do not wish to be bound, however, by any theoretical explanation of the mechanism by which the superior oral bioavailability of the present formulation is achieved.

Polyethylene glycol having a molecular weight of from 200 to 400 has been chosen as the vehicle for the present composition. Polyethylene glycol has the necessary solvent capability for etoposide and exhibits acceptable viscosity and dispersibility in water to meet the requirements of the present invention. Polyethylene glycol having molecular weight of from 200 to 300 is preferred because it is less viscous than polyethylene glycol 400. The lower viscosity facilitates manufacturing manipulations, and increases the dispersibility of the composition on mixing with water or gastric contents. Other ingredients of the composition serve to improve dispersibility and to facilitate micelle formation on mixing thereof with water, or to improve compatibility of the solution with the capsule shell when the material is encapsulated in a soft gelatin capsule according to a preferred embodiment of the invention.

From 5 to 9 parts by weight of polyethylene glycol 300 per part by weight of etoposide is preferably employed. Within this range the rate of solution of the etoposide is sufficient for manufacturing convenience, a sufficiently fluid mixture is obtained for convenient handling, and the solution is sufficiently concentrated so that a unit dosage form may be contained in a sufficiently small volume of solution to permit encapsulation within a soft gelatin capsule. More dilute solutions may, of course, be prepared for dropper or teaspoon dosage use. Such is also contemplated by the present invention.

The etoposide is preferably micronized prior to formulation into the present composition, but this is primarily a convenience and not a necessity since a true solution of etoposide in the polyethylene glycol is formed. Ordinarily when etoposide is dissolved in a water soluble organic solvent, and the resulting solution mixed with water, the etoposide precipitates because of its very low water solubility. According to the present invention, taurocholic acid is included in the composition and the presence of this ingredient results, presumably, in the formation of a micellar solution when the composition is mixed with water.

Other bile acids will similarly promote the formation of apparent micellar solutions on mixing of the polyethylene glycol solution with water, but they are unsuited for use in the present compositions since the so-produced micellar solutions are unstable or do not form at acid pH. Sodium deoxycholate or sodium cholate form micellar solutions with etoposide, but the micellar solutions have pH values of pH 10.9 and pH 11.0 respectively. Upon acidification, the etoposide precipitates from such solutions. Such are not therefor suitable for ingestion due to the acidic nature of the gastric contents. Furthermore, for encapsulation within a soft gelatin capsule shell an acidic pH is preferred because the gelatin shell is disrupted by fill-solutions having pH values in excess of pH 8.0. It has been found by empirical experimentation that preferably about 3.5 parts by weight of taurocholic acid per part by weight of etoposide are desirable to provide a stable micellar solution on dilution of the composition with water. Smaller amounts such as 2.0 parts by weight, and larger amounts of taurocholic acid may be employed. No useful purpose is served by using more than about 10 parts by weight of taurocholic acid per part by weight of etoposide.

A water soluble acid is included in the composition to assure that an acidic pH value is obtained upon dilution to form the micellar solution. For purposes of pharmaceutical elegance and ease of handling in a manufacturing operation, we prefer to use a solid water-soluble organic carboxylic acid, but other acids may be employed. We prefer maleic, tartaric, citric, gluconic, or ascorbic acids which are water-soluble, non-toxic and convenient to handle in a pharmaceutical manufacturing operation. Most preferred is citric acid which we have found to be appropriate when used in from 0.1 to 0.5 parts by weight per part by weight of etoposide. The most preferred proportion is 0.2 parts by weight of citric acid per part by weight of etoposide.

Ethanol serves the important purpose in the composition of promoting rapid dispersion on mixing with water and facilitates formation of the micellar solution. Other water-soluble polar organic solvents such as methanol, propanol, acetone, etc. which are also effective are not suitable for ingestion and, accordingly, ethanol has been selected for this purpose. At least 5% by weight of the composition of ethanol is necessary for this purpose, but higher amounts up to 20% by weight may be used, particularly for purposes of a dropper or teaspoon dosage form. For encapsulation within a soft gelatin capsule, a maximum of 10% by weight of ethanol in the composition may be used. Solutions having higher concentrations of ethanol than 10% by weight may cause dehydration of the gelatin capsule wall and hence may not be suitable for encapsulation with this type of a capsule.

Finally, for use of the present composition in a unit dose form contained within a soft gelatin capsule it is desirable to include up to about one part by weight of water per part by weight of etoposide to improve the compatibility of the composition with the soft gelatin capsule shell. The hydrophilic nature of polyethyleneglycol, ethanol, citric acid, and taurocholic acid causes the composition to abstract the water from the capsule shell and may cause it rupture on prolonged storage. Sufficient water is therefore included in the composition, preferably one part by weight of water per part by weight of etoposide, to render the composition compatible with the capsule shell and prevent dehydration thereof. It is desirable to select an amount of water which will confer stability for a storage period of two years at room temperature when the capsules are stored in a closed container.

The preferred embodiments of the present invention are stable, liquid compositions in the form of true solutions having the following composition:

| Ingredient | Parts by Weight |
| --- | --- |
| polyethanol glycol 300 | 5 to 9 |
| etoposide | 1 |
| citric acid | 0.1 to 0.5 |
| taurocholic acid | 2.0 to 10 |
| ethanol | 5 to 20% by weight of total solution weight |

The most preferred embodiment of the present invention is the following composition:

| Ingredient | Parts by Weight |
| --- | --- |
| polyethylene glycol 300 | 6.8 |
| etoposide, micronized | 1.0 |
| citric acid | 0.2 |
| ethanol | 1.0 |
| taurocholic acid | 3.5 |
| water | 1.0 |

The following example constitutes a description of the preferred composition of the present invention.

EXAMPLE

The following ingredient were weighed:

| | |
| --- | --- |
| Etoposide | 25.0 g |
| Citric Acid, Anhydrous, USP | 5.0 g |
| Polyethylene glycol 300 | 170.0 g |
| Alcohol, USP | 25.0 g |
| Taurocholic Acid | 87.5 g |
| Purified Water, USP | 25.0 g |

The taurocholic acid is added portionwise to the polyethylene glycol 300 with stirring to form a suspension. The water is then added followed by the alcohol and citric acid. A solution forms which is warmed to 65° C., allowed to cool to 35° C., and filtered (Millipore AP 25 29325). An atmosphere of nitrogen is maintained over the solution during those steps. The filtrate is kept at 30°–35° C., and the etoposide is then dissolved therein. The solution is then assayed (found 71.3 mg/g of etoposide) and filled into soft gelatin capsules at 100 mg etoposide per capsule.

The foregoing capsule-fill solution has the following characteristics, and stability.

CHARACTERISTICS

| | CHARACTERISTICS | |
| --- | --- | --- |
| 1. | Color | Dark Brown |
| 2. | pH | 4.6 |
| 3. | Viscosity | Satisfactory |
| 4. | Dispersibility | Easily dispersible |
| 5. | Shell Compatibility, Physical | Compatible |
| 6. | Precipitation formation time on dilution with H2O to 1:1, 1:5, 1:10 and 1:100 | >3 hours |

STABILITY

| STABILITY | | |
| --- | --- | --- |
| Storage Temperature | Storage Time (Days) | % Remaining |
| 4° C. (Control) | 8 | 100 |
| 70° C. | 5 | 102 |
| 70° C. | 8 | 102 |
| 56° C. | 8 | 102 |
| 37° C. | 8 | 105 |
| 25° C. | 8 | 99 |

What is claimed is:

1. A pharmaceutical solution dosage composition adapted for the oral adminstration of etoposide comprising (a) about 1 part by weight of etoposite, and on the basis of parts by weight per part of etoposide, (b) 5 to 9 parts by weight of polyethylene glycol, (c) 2.0 to 10 parts by weight of taurocholic acid, (d) 5% to 20% by weight of total solution ethanol, and (e) 0.1 to 0.5 parts by weight of an additional water-soluble organic carboxylic acid in such proportion as to form a homogeneous solution which is stable and free of precipitate and is acidic after dilution with water for a period of time sufficient to permit oral administration of said pharmaceutical dosage composition and absorption of the contents by a mammalian organism.

2. The composition of claim 1 in dosage unit form wherein said homogeneous liquid is contained within a soft gelatin capsule.

3. The composition of claim 2 wherein said dosage unit contains from 10 mg. to 100 mg. of etoposide.

4. The composition of claim 2 wherein said homogeneous liquid also contains water in an amount sufficient to prevent dehydration of the capsule shell and to render said shell stable during a storage period of at least 2 years at room temperature in a closed container.

5. The composition of claim 1 wherein the molecular weight of the polyethylene glycol is within the range of about 200 to 400.

6. The composition of claim 1 wherein the molecular weight of the polyethylene glycol is about 300.

7. The composition of claim 1 wherein said water soluble acid is citric acid.

8. The composition of claim 1 wherein 3.5 parts by weight of taurocholic acid per part by weight of etoposide is employed.

9. The composition of claim 1 comprising a solution adapted for encapsulation with in a soft gelatin shell and having the following composition:

| Ingredient | Parts by Weight |
| --- | --- |
| polyethylene glycol 300 | 6.8 |
| etoposide, micronized | 1.0 |
| citric acid | 0.2 |
| ethanol | 1.0 |
| taurocholic acid | 3.5 |
| water | 1.0 |

10. A method for enhancing the bioavailability of etoposide contained in a pharamceutical solution dosage composition also containing polyethylene glycol, citric acid and water comprising combining therewith taurocholic acid and ethanol in amounts sufficient to provide a composition having the following formulation:

| Ingredient | Parts by Weight |
| --- | --- |
| polyethylene glycol | 5 to 9 |
| etoposide | 1 |
| citric acid | 0.1 to 0.5 |
| taurocholic acid | 2.0 to 10 |
| ethanol | 5 to 20% by weight of total solution weight. |

11. The method of claim 10 wherein ssaid composition further contains up to about 1 part of water per part by weight of etoposide.

* * * * *